United States Patent [19]
Chen et al.

[11] Patent Number: 5,922,352
[45] Date of Patent: Jul. 13, 1999

[54] ONCE DAILY CALCIUM CHANNEL BLOCKER TABLET HAVING A DELAYED RELEASE CORE

[75] Inventors: Chih-Ming Chen, Davie; Joseph C.H. Chou, Coral Springs, both of Fla.

[73] Assignee: ANDRX Pharmaceuticals, Inc., Fort Lauderdale, Fla.

[21] Appl. No.: 08/792,001

[22] Filed: Jan. 31, 1997

[51] Int. Cl.$^6$ ..................................................... A61K 9/20
[52] U.S. Cl. .......................... 424/465; 424/489; 424/476
[58] Field of Search ................................... 424/465, 489, 424/476

[56] References Cited

U.S. PATENT DOCUMENTS

| | | |
|---|---|---|
| 4,327,725 | 5/1982 | Cortese et al. . |
| 4,412,986 | 11/1983 | Kawata et al. . |
| 4,503,030 | 3/1985 | Edgren et al. . |
| 4,562,069 | 12/1985 | Hegasy et al. . |
| 4,587,117 | 5/1986 | Edgren et al. . |
| 4,612,008 | 9/1986 | Wong et al. . |
| 4,765,989 | 8/1988 | Wong et al. . |
| 4,765,990 | 8/1988 | Sugimoto et al. . |
| 4,783,337 | 11/1988 | Wong et al. . |
| 4,792,448 | 12/1988 | Ranade . |
| 4,808,413 | 2/1989 | Joshi et al. . |
| 4,867,985 | 9/1989 | Heafield et al. . |
| 4,880,623 | 11/1989 | Piergiorgio et al. . |
| 4,882,114 | 11/1989 | Hegasy . |
| 4,892,730 | 1/1990 | Hegasy . |
| 4,892,741 | 1/1990 | Ohm et al. . |
| 4,952,402 | 8/1990 | Sparks et al. . |
| 4,966,772 | 10/1990 | Ohm et al. . |
| 4,973,469 | 11/1990 | Mulligan et al. . |
| 4,981,683 | 1/1991 | Hegasy . |
| 5,007,790 | 4/1991 | Shell . |
| 5,015,479 | 5/1991 | Mulligan et al. . |
| 5,051,263 | 9/1991 | Barry et al. . |
| 5,055,306 | 10/1991 | Barry et al. . |
| 5,071,642 | 12/1991 | Lahr et al. . |
| 5,108,757 | 4/1992 | Erdos et al. . |
| 5,128,142 | 7/1992 | Mulligan et al. . |
| 5,145,683 | 9/1992 | Rhodes . |
| 5,160,734 | 11/1992 | Ganesan et al. . |
| 5,190,765 | 3/1993 | Jao et al. . |
| 5,204,121 | 4/1993 | Bücheler et al. . |
| 5,208,037 | 5/1993 | Wright et al. . |
| 5,264,446 | 11/1993 | Hegasy et al. . |
| 5,266,581 | 11/1993 | Schmidt et al. . |
| 5,326,571 | 7/1994 | Wright et al. . |
| 5,430,021 | 7/1995 | Rudnic et al. . |
| 5,439,687 | 8/1995 | Compassi . |
| 5,447,729 | 9/1995 | Belenduik et al. . |
| 5,500,227 | 3/1996 | Oshlack et al. ........................ 424/476 |
| 5,543,099 | 8/1996 | Zhang et al. . |
| 5,543,154 | 8/1996 | Rork et al. . |
| 5,543,155 | 8/1996 | Fekete et al. . |
| 5,582,838 | 12/1996 | Rork et al. . |
| 5,594,013 | 1/1997 | Trigger . |

FOREIGN PATENT DOCUMENTS 1456618  11/1976  United Kingdom .

*Primary Examiner*—Thurman K. Page
*Assistant Examiner*—William E. Benston, Jr.
*Attorney, Agent, or Firm*—Hedman, Gibson, Costigan, P.C.

[57] ABSTRACT

A controlled release dosage form which comprises:
(a) a homogeneous compressed core which comprises a compressed granulation of:
  (i) particles of a calcium channel blocker compound coated with an enteric polymer that are dispersed onto a solid pharmaceutical filler; and
(b) a continuous compressed outer layer around said homogeneous compressed core which comprises a compressed granulation of:
  (i) one or more pharmaceutically acceptable polymers which form a hydrogel in which calcium channel blocker compound is dispersed.

9 Claims, 3 Drawing Sheets

ONCE DAILY CALCIUM CHANNEL BLOCKER TABLET HAVING A DELAYED RELEASE CORE

BACKGROUND OF THE INVENTION:

The present invention relates to controlled release unit dose formulations of pharmaceuticals. In the prior art, many techniques have been used to provide controlled and extended-release pharmaceutical dosage forms in order to maintain therapeutic serum levels of medicaments and to minimize the effects of missed doses of drugs caused by a lack of patient compliance.

In the prior art, extended release tablets containing the calcium channel blocker nifedipine have been described which were based on the use of a rapid release core component that was covered by a secondary layer which contained nifedipine in a form which released the nifedipine at a slower rate than the core. The rapid release core is described as being capable of releasing at least 75% of the active drug in not less than one hour in a medium of 0.5% sodium lauryl sulfate/0.1N HCl. A product of this type is sold commercially as Adalat CC®. U.S. Pat. No. 4,892,741 discloses a press coated tablet for administering nifedipine. The core of this tablet contains a rapid release form of nifedipine and the outer coat around the core contains a dihydropyridine in slow release form.

Other extended release nifedipine dosage forms have been described in which the core is divided into two layers (compositions) one of which contains the active drug and the other contains a push layer of pharmacologically inactive ingredients which are osmotically active in the presence of gastrointestinal fluids. An outer water permeable coating covers the tablet which is provided with an aperture that is formed by laser drilled orifice to allow the medicament to be extruded out of the drug layer. A product of this type is disclosed in U.S. Pat. Nos. 4,783,337; 4,765,989; 4,612,008; and 4,327,725 and is sold commercially as Procardia XL®. Other controlled release compositions include those described in U.S. Pat. No. 3,948,254 and U.S. Pat. No. 4,036,227.

The osmotic dosage forms that are disclosed in U.S. Pat. No. 4,783,337 are described as having a passageway which includes an aperture, orifice, hole, porous element, hollow fiber, capillary tube, microporous insert, pore, microporous overlay or bore which extends through the semipermeable lamina wall into a drug layer. The patent also states that the passageway may be formed by mechanical drilling, laser drilling, eroding an erodible element, extracting, dissolving, bursting or leaching a passageway-former from the wall of the osmotic dosage form (col. 14, line 35 et seq.) which are pre-formed in the tablet during the manufacturing process. The only exemplified technique of forming a passageway in U.S. Pat. No. 4,783,337 is the use of a laser to drill a hole in the outer layer of the tablet and the dosage forms are all based on a drug layer superimposed on a secondary layer.

U.S. Pat. No. 4,285,987 describes an osmotic tablet which had a laser drilled aperture into the core of the tablet. The laser drilled hole was plugged with leachable sorbitol which was leached out in the presence of gastrointestinal fluid.

The present invention is concerned with providing a once a day tablet containing a calcium channel blocker tablet that does not have a rapid release core but is provided with a core having delayed release properties which contains an enteric coated calcium channel blocker compound which is prepared by mixing the calcium channel blocker with an enteric polymer in an aqueous medium and dispersing that mixture onto a solid pharmaceutical diluent to form a granulation.

SUMMARY OF THE INVENTION

The present invention is directed to a controlled release dosage form which comprises:

(a) a homogeneous compressed core which comprises a compressed granulation of:
  (i) particles of a calcium channel blocker compound coated with an enteric polymer that are dispersed onto a solid pharmaceutical filler; and (b) a continuous compressed outer layer around said homogeneous compressed core which comprises a compressed granulation of:
  (i) one or more pharmaceutically acceptable polymers which form a hydrogel in which a calcium channel blocker compound is dispersed.

It is an object of the invention to provide a once a day formulation of a calcium channel blocker.

It is also an object of the present invention to provide a controlled release pharmaceutical tablet that does not require an osmotic core.

It is also an object of this invention to provide a controlled release pharmaceutical tablet having an inner compressed core and an outer compressed coat which may be made using ordinary tablet compression techniques.

These and other objects of the invention will become apparent from the appended specification.

DETAILED DESCRIPTION OF THE INVENTION

Figure 1:
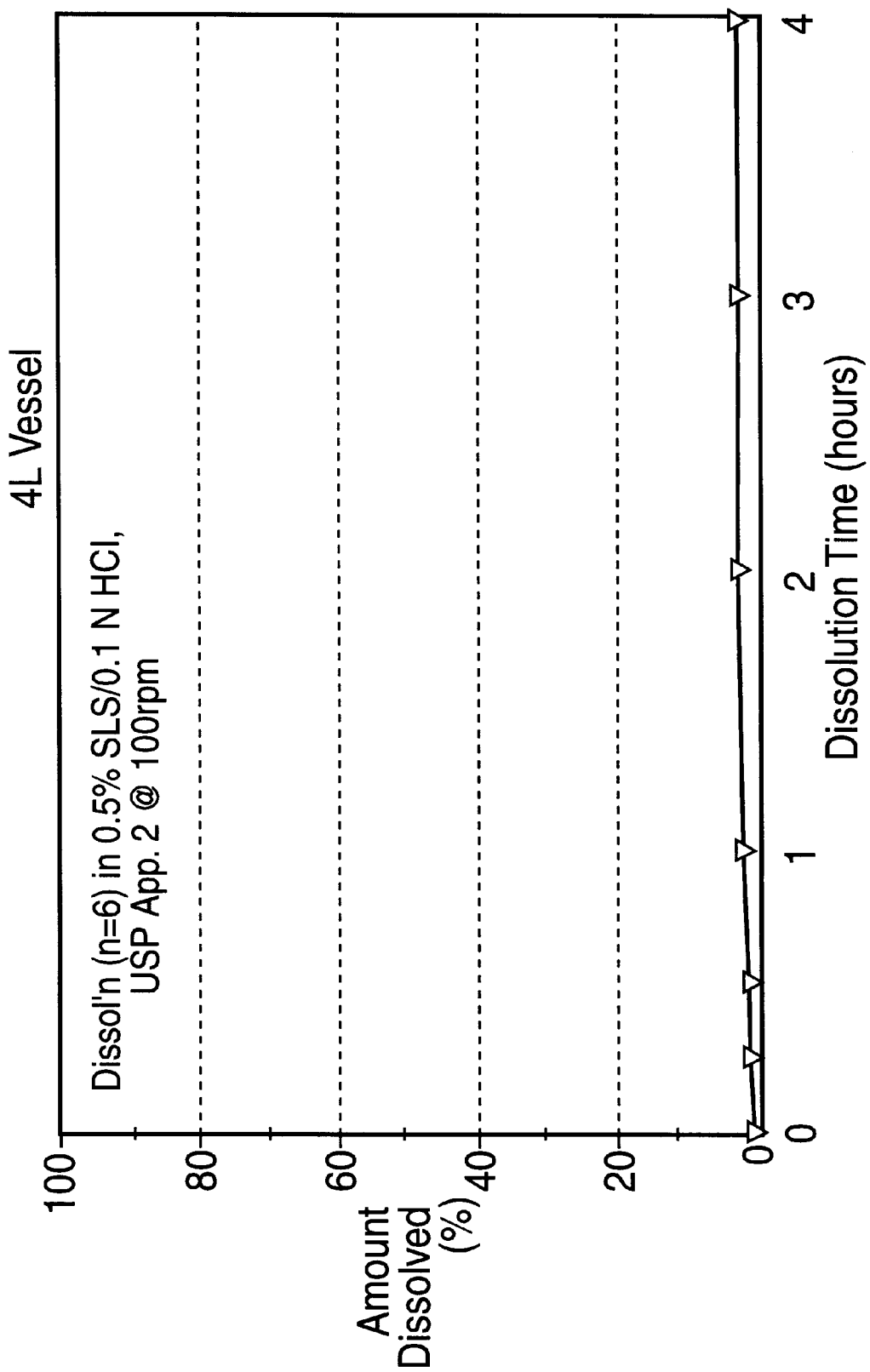
FIG. 1 is a graph which shows the dissolution profile of a nifedipine core tablet of the invention in 0.5% sodium lauryl sulfate/0.1N HCl at 37° C. in a type 2 USP apparatus.
Figure 2:
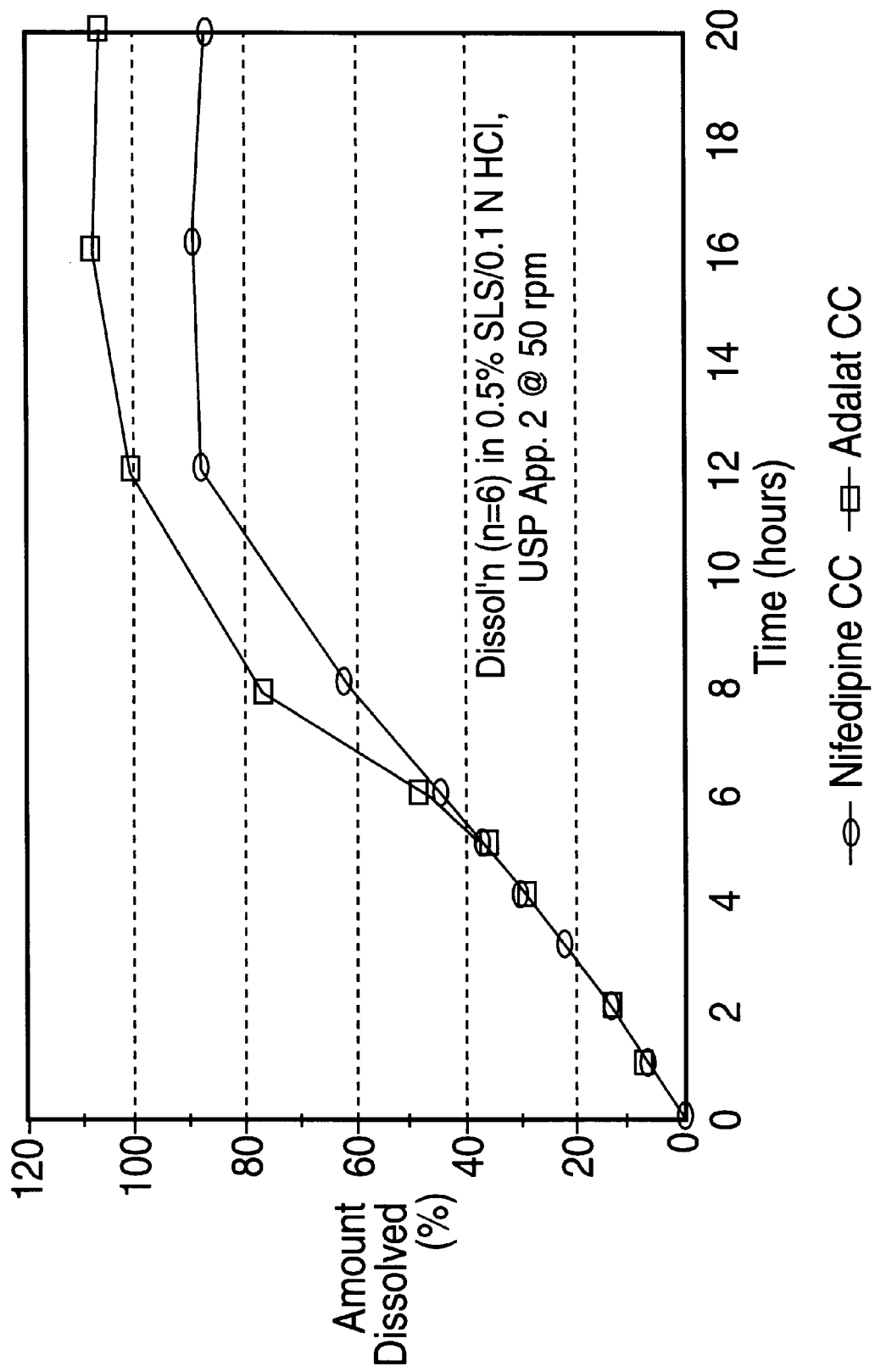
FIG. 2 is a graph of data which compares the dissolution profile of a tablet according to Example 1 with the dissolution profile of the commercial product AdalatCC® in 0.5% sodium lauryl sulfate/0.1N HCl at 37° C. in a type 2 USP apparatus.
Figure 3:
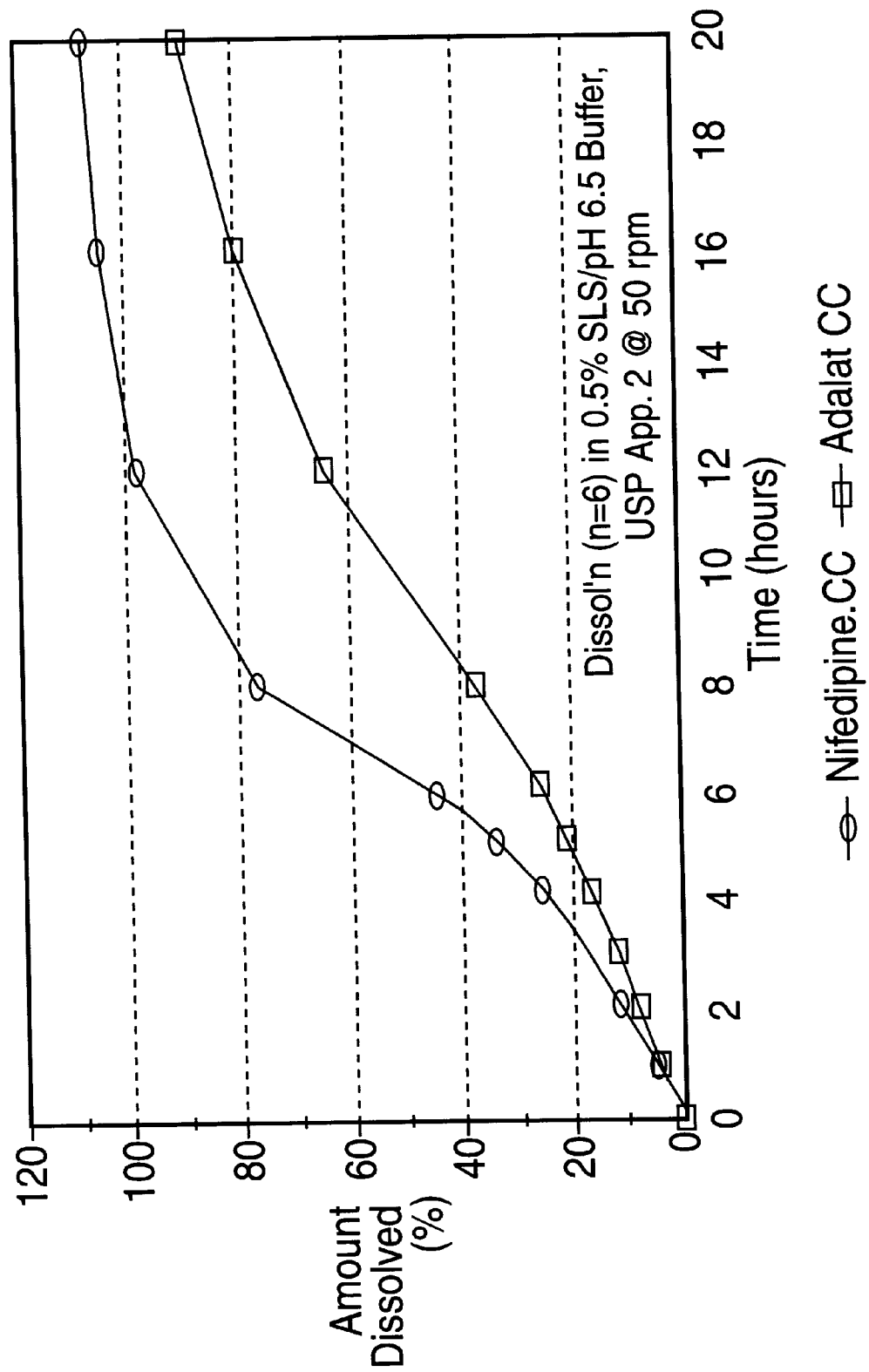
FIG. 3 is a graph of data which shows the dissolution profile of the tablet according to Example 1 in 0.5% sodium lauryl sulfate/pH6.5 buffer, at 37° C. in a type 2 USP apparatus.

The tablet of the invention has a delayed release core and an outer extended release coating which provides bioequivalent pharmacokinetic performance (i.e., maintains a sustained 24 hour drug plasma level) for a calcium channel blocker when compared with the commercially available Adalat CC tablet which contains the calcium channel blocker nifedipine and has a rapid release core and a extended release external coat.

In the tablets of the invention, generally the total amount of the calcium channel blocker is a sufficient amount to provide a 24 hour therapeutic effect of the calcium channel blocker compound by the ingestion of one single dosage unit. This amount may be from 30 to 90 mg per dosage unit.

The core of the controlled release tablet of the present invention contains a micronized crystalline calcium channel blocker. The micronized crystalline calcium channel blocker such as nifedipine is combined with an enteric coating agent which may contain a suitable plasticizer and a solid pharmaceutical acceptable filler or solid diluent. A preferred micronized nifedipine will have a surface area of 5 $m^2$/g or higher.

The enteric polymers which may be used include Eudragit S (methacrylic acid/methyl methacrylate copolymer with a 1:2 ratio of MA to MMA) or Eudragit L (methacrylic acid/methyl methacrylate copolymer with a 1:1 ratio of MA to MMA), hydroxypropylmethylcellulose phthalate (HPMCP), cellulose acetate phthalate, shellac etc. A granulation is formed of the enteric coated calcium channel blocker compound and this granulation is compressed into a tablet which is used as the delayed releasing core of the tablet of the invention. The granules which form the compressed core may contain a pharmaceutically acceptable diluent in addition to the calcium channel blocker compound. The granulation for the core may also include a binder which may be a film forming polymer such as polyvinylpyrrolidone or microcrystalline cellulose as well as tablet disintegrating agents such as croscarmellose sodium, sodium starch glycolate, crospovidone, polacrilin potassium and the like as well as a tablet lubricant such as glyceryl monostearate, magnesium stearate and stearic acid.

The pharmaceutically acceptable fillers include solid pharmaceutical diluents such as hydroxypropyl cellulose, lactose, sucrose, dextrose, sodium chloride, potassium chloride, microcrystalline cellulose and the like.

The core of the tabletted dosage form of the invention is provided with an external layer of an extended release formulation which also contains the calcium channel blocker compound. The external coat is formed by compressing the granules around the delayed release core to form an extended release external layer. The external coat of the extended release formulation will contain effective amounts of a pharmaceutically acceptable polymer which forms a hydrogel as well as tablet lubricants.

Examples of pharmaceutically acceptable polymers which form a hydrogel include hydroxypropyl cellulose, hydroxypropylmethyl cellulose, polyethylene oxide having a weight average molecular weight of 100,000 to 6,000,000, poly(hydroxy alkyl methacrylate) having a molecular weight of from 30,000 to 5,000,000; poly(vinyl)alcohol, having a low acetal residue, which is cross-linked with glyoxal, formaldehyde or glutaraldehyde and having a degree of polymerization of from 200 to 30,000; a mixture of methyl cellulose, cross-linked agar and carboxymethyl cellulose; a hydrogel forming copolymer produced by forming a dispersion of a finely divided copolymer of maleic anhydride with styrene, ethylene, propylene, butylene or isobutylene cross-linked with from 0.001 to 0.5 moles of saturated cross-linking agent per mole of maleic anyhydride in the copolymer; Carbopol® acidic carboxy polymers having a molecular weight of 450,000 to 4,000,000; Cyanamer® polyacrylamides; cross-linked water swellable indenemaleic anhydride polymers; Goodrite® polyacrylic acid having a molecular weight of 80,000 to 200,000; starch graft copolymers; Aqua-Keeps® acrylate polymer polysaccharides composed of condensed glucose units such as diester cross-linked polyglucan and the like. Other polymers which form hydrogels are described in U.S. Pat. No. 3,865,108; U.S. Pat. No. 4,002,173 and U.S. Pat. No. 4,207,893 all of which are incorporated by reference.

A tabletting machine may be used to compress the granulation mixture into a core tablet having a homogeneous core. The homogeneous core is subsequently completely covered with a compressed outer layer which may be compressed around the core by using a conventional apparatus such as a Dri-Cota tabletting machine.

The controlled release tablet of the invention is primarily intended to be used to administer calcium channel blockers such as the dihydropyridines which are slightly soluble to practically insoluble in water although other water soluble calcium channel blocking agents may be employed. The terms slightly soluble to practically insoluble are used to include those substances which are soluble in from 100 to more than 10,000 parts of water per part of solute.

Specific examples of dihydropyridine calcium channel blockers include nifedipine, nisoldipine, nicardipine, nitredipine, nilvadipine, felodipine and the like. Other calcium channel blocking agents which may be used include verapamil and diltiazem.

After the external coat is compressed around the tablet core, a final film coating is applied which may be a protective seal coat which is applied by means of a conventional sugar or polymeric film coating solution which is applied in a coating pan. The outer coat should protect the light sensitive calcium channel blocking agent from any light source which will affect the calcium channel blocking agent. A composition of Opadry Yellow and sodium chloride (90%–10% to 10%–90%) which is applied from a water based system may be used to coat the tablets of the invention. Opadry yellow contains hydroxypropylmethyl cellulose; titanium dioxide; polyethylene glycol 4000; polysorbate 80; D&C yellow No.10 aluminum lake; and FD&C red #40 aluminum lake. These coatings may also contain a minor amount e.g. 2–5% of a water swellable polymer such as hydroxypropylmethyl cellulose or a polyethylene oxide polymer having a molecular weight of 200,000 to 1,000,000 (wt.av.). These coatings may be applied in the form of a suspension by using a perforated coating pan.

Generally, the final film coating around the outer layer will comprise from about 1 to 5% preferably about 2 to 3% based on the total weight of the tablet.

In the preparation of the tablets of the invention, various conventional well known solvents may be used to prepare the granules and apply the external coating to the tablets of the invention. In addition, various diluents, excipients, lubricants, dyes, pigments, dispersants etc. which are disclosed in Remington's Pharmaceutical Sciences, 1995 Edition may be used to optimize the formulations of the invention. In the alternative, dry granulation techniques may be used to prepare formulation for making compressed tablets.

Generally the tablet of the invention will comprise the following materials:

(a) 10% to 30%, and preferably 15% to 25% of a homogeneous compressed core which comprises a compressed granulation of:
  (i) 5% to 40%, and preferably 10% to 30% of particles of a calcium channel blocker compound coated with an amount of an enteric polymer which provides delayed release properties to the core;
  (ii) 95% to 60%, and preferably 90% to 70% of a solid pharmaceutically acceptable filler;
  (iii) 0% to 3%, and preferably 1% to 2% of a tablet lubricant;
  (iv) 0% to 5%, and preferably 1% to 3% of a tablet disintegrating agent; and
(b) 90% to 70%, and preferably 85% to 75% of a compressed outer layer around said homogeneous compressed core which comprises a granulation of:
  (i) 90% to 50%, and more preferably 60% to 80% of one or more pharmaceutically acceptable polymers which form a hydrogel having from 50% to 40% and preferably 10% to 30% of a dispersed calcium channel blocker; and
  (ii) 0% to 30% and preferably from 10% to 20% a pharmaceutically acceptable filler.

DESCRIPTION OF THE PREFERRED EMBODIMENTS

EXAMPLE 1

Tablets having the following formula are prepared as follows:

| I Core Tablet Granulation | |
|---|---|
| nifedipine (micronized crystalline 5.8 m²/g) | 715 g |
| hydroxypropyl methyl cellulose phthalate[1] | 720 g |
| sodium hydroxide | 68 g |
| triacetin | 715 g |
| lactose (anhydrous) | 4377 g |
| water | 14.4 kg |

[1]weight average molecular weight = 78,000;

(a) The crystalline nifedipine is first dispersed in a solution of the hydroxypropyl methylcellulose phthalate, the sodium hydroxide and triacetin in the water. This dispersion is then formed into a granulation using a fluidized bed. The dried granules are sized and mixed with 214 g of polyvinylpyrrolidone, 286 g of croscarmellose sodium and 71 g of glyceryl monostearate. Core tablets weighing 50 mg and having a diameter of 0.2 inches are prepared using direct compression.

| II Coating granules | |
|---|---|
| hydroxypropyl cellulose (Klucel EF) | 2245 g |
| nifedipine (micronized crystalline 5.8 m²/g) | 408 g |
| hydroxypropyl cellulose (Klucel HXF) | 612 g |
| anhydrous lactose | 735 g |
| glyceryl monostearate | 82 g |
| purified water | 2 kg |

A 102 g portion of the hydroxypropyl cellulose (Klucel EF) is dissolved in 2 kg of water and the nifedipine is dispersed into the solution to form a granulating suspension. A mixture of 612 g of hydroxypropyl cellulose (Klucel HXF), 2143 g of hydroxypropyl cellulose (Klucel EF) and 735 g of anhydrous lactose were granulated in a fluidized bed. The dried granulation is sized and mixed with 82 g of glyceryl monostearate.

III Final Tablet

The core tablet (50 mg) is combined with the coating granules (250 mg) in a press coater (Dri-Cota) and 300 mg tablets having a diameter of 0.341 inches are compressed. These tablets are then coated with:

| Opadry Yellow[4] | 75% |
|---|---|
| sodium chloride | 25% |
| water qs(evaporated during processing) | |

[4]hydroxypropylmethyl cellulose; titanium dioxide; polyethylene glycol 4000; polysorbate 80; D&C yellow No. 10 aluminum lake; and FD&C red #40 aluminum lake The yellow color suspension is applied to the previously prepared tablets in a perforated coating pan. The coating level is 4% by weight.

The color coating is to protect the drug from light.

The term "%" as used herein refers to weight percent.

Two pilot biostudies were carried out to compare the tablet of Example 1 with the commercial product AdalatCC under fasting and fed conditions. The following results were obtained:

| | | At 90% Confidence Interval | |
|---|---|---|---|
| | Geometric Mean Ratio | Lower Limit | Upper Limit |
| Fasting Subjects (n = 6) | | | |
| AUC 0-t | 1.088 | 94.35% | 125.51% |
| AUC 0-24 | 1.076 | 95.41% | 121.28% |
| Cmax | 1.195 | 107.47% | 132.98% |
| Fed Subjects (n = 6) | | | |
| AUC 0-t | 1.028 | | |
| AUC 0-24 | 1.020 | | |
| C-Max | 1.168 | | |

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

We claim:

1. A controlled release dosage form which comprises:
   (a) a delayed release homogeneous compressed core which comprises a compressed granulation of:
      (i) particles of a calcium channel blocker compound coated with an enteric polymer that are dispersed onto a solid pharmaceutical filler; and
   (b) a continuous compressed outer layer around said homogeneous compressed core which comprises a compressed granulation of:
      (i) one or more pharmaceutically acceptable polymers which form a hydrogel in which calcium channel blocker compound is dispersed.

2. A controlled release pharmaceutical tablet as defined in claim 1 wherein the calcium channel blocker is nifedipine.

3. A controlled release pharmaceutical tablet as defined in claim 2 wherein the enteric polymer is selected from the group consisting of hydroxypropylmethylcellulose phthalate, cellulose acetate phthalate, shellac and polymethyl methacrylate copolymers.

4. A controlled release pharmaceutical tablet as defined in claim 3 wherein the enteric coating is plasticized with a plasticizer.

5. A controlled release pharmaceutical tablet as defined in claim 4 wherein the enteric coating is plasticized with triacetin.

6. A controlled release pharmaceutical tablet as defined in claim 1 wherein the pharmaceutically acceptable polymer which forms a hydrogel is hydroxypropyl cellulose.

7. A controlled release pharmaceutical tablet which consists essentially of
   (a) a delayed release homogeneous compressed core which consists essentially of a compressed granulation of:
      (i) particles of nifedipine coated with hydroxypropylmethyl cellulose phthalate which is dispersed on an anhydrous lactose; and
   (b) a continuous extended release compressed outer core layer around said homogeneous compressed core which consists essentially of a compressed granulation of:

(i) hydroxypropyl cellulose;
(ii) nifedipine; and
(iii) anhydrous lactose.

8. A controlled release pharmaceutical tablet as defined in claim 7 wherein the core contains a tablet lubricant.

9. A controlled release dosage form which consists essentially of:
  (a) a delayed release homogeneous compressed core which consists essentially of a compressed granulation of:
    (i) particles of a calcium channel blocker compound coated with an enteric polymer that are dispersed onto a solid pharmaceutical filler; and
  (b) a continuous compressed outer layer around said homogeneous compressed core which consists essentially of a compressed granulation of:
    (i) one or more pharmaceutically acceptable polymers which form a hydrogel in which calcium channel blocker compound is dispersed.

* * * * *